(12) United States Patent
Habicher et al.

(10) Patent No.: US 7,582,469 B2
(45) Date of Patent: Sep. 1, 2009

(54) METHOD FOR ENANTIOSELECTIVELY OPENING OXETAN-2-ONES

(75) Inventors: Tilo Habicher, Speyer (DE); Rainer Stürmer, Rödersheim-Gronau (DE)

(73) Assignee: BASF SE, Ludwigshafen (DE)

( * ) Notice: Subject to any disclaimer, the term of this patent is extended or adjusted under 35 U.S.C. 154(b) by 436 days.

(21) Appl. No.: 11/659,139

(22) PCT Filed: Jul. 28, 2005

(86) PCT No.: PCT/EP2005/008190

§ 371 (c)(1),
(2), (4) Date: Feb. 1, 2007

(87) PCT Pub. No.: WO2006/015727

PCT Pub. Date: Feb. 16, 2006

(65) Prior Publication Data

US 2008/0311633 A1 Dec. 18, 2008

(30) Foreign Application Priority Data

Aug. 2, 2004 (DE) ........................ 10 2004 037 700
Aug. 6, 2004 (DE) ........................ 10 2004 038 589

(51) Int. Cl.
*C12P 41/00* (2006.01)
(52) U.S. Cl. ................................... 435/280
(58) Field of Classification Search ................ None
See application file for complete search history.

(56) References Cited

FOREIGN PATENT DOCUMENTS

WO WO-97/13763 4/1997

OTHER PUBLICATIONS

Koichi et al., "Lipase-promoted asymmetric transesterification of 4-alkyloxetan-2-ones with ring opening", J. Chem. Soc. Perkin Trans. 1 : 1645-1646 (1995).*
Sakai, N., et al., "Lipase promoted asymmetric trans-esterification of 4-alkyl-,3-alkyl- and 3,4-dialkyloxetan-2-ones with ring-opening" J. Chem. Soc., Perkin Trans. 1, 2000, pp. 71-77.
Adam, W., et al., "Enzymatic preparation of optically active α-methylene β-lactones by lipase-catalyzed kinetic resolution through asymmetric transesterification," Tetrahedron: Assymmetry, vol. 8, No. 6, 1997, pp. 833-836.
Ito, T., et al., "Preparation and Use of Novel (S)-β-Chlorodifluoromethyl-β-propiolactone as a Chiral Fluorinated Building Block," Tetrahedron, vol. 54, 1998, pp. 5523-5530.
Burk, M., et al., "Highly Enantioselective Hydrogenation of β-Keto Esters under Mild Conditions," J. Am. Chem. Soc., 1995, 117, 4423.
Mortreux, A., et al., "Rhodium(I) Bis(aminophosphane) Complexes as Catalysts for Asymmetric Hydrogenation of Activated Ketones," Tetrahedron: Asymmetry, vol. 7, No. 2, 1996, pp. 379-382.
Haack, K., et al., "The Catalyst Precursor, Catalyst, and Intermediate in the $Ru^{II}$-Promoted Asymmetric Hydrogen Transfer between Alcohols and Ketones," Angew. Chem. Int. Ed. Engl., vol. 36, No. 3, 1997, pp. 285-288.
Knochel, P., et al., "New Efficient Catalysts for Enantioselective Transfer Hydrogenations," Tetrahedron Lett., vol. 37, No. 45, 1996, pp. 8165-8168.
Sammakia, T., et al., "Transfer Hydrogenation with Ruthenium Complexes of Chiral (Phosphinoferrocenyl) oxazolines," J. Org. Chem., vol. 62, No. 18, 1997, pp. 6104-6105.

* cited by examiner

*Primary Examiner*—Sandra E. Saucier
(74) *Attorney, Agent, or Firm*—Connolly Bove Lodge & Hutz LLP

(57) ABSTRACT

A method for preparing substantially enantiopure 3-hydroxy carboxylic acids or esters of the general formula (III) by reacting racemic oxetan-2-ones of the general formula (I) with compounds R3-OH of the general formula (II) in the presence of a lipase from *Candida antartica* or *Burkholderia plantarii*, and separating the resulting products of the formula (III) and (IV) from one another

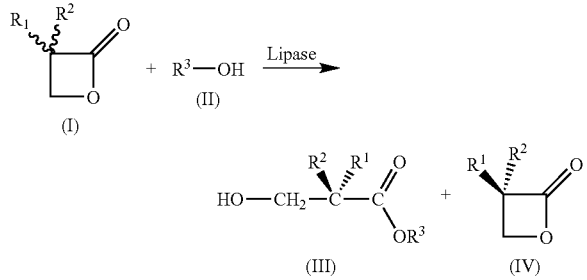

where the radicals have the following meaning:
$R^1$, $R^2$, $R^3$ independently of one another H; $C_1$-$C_{10}$-substituted or unsubstituted alkyl, substituted or unsubstituted aryl or hetaryl, where $R^1$ and $R^2$ may not simultaneously have the same meaning.

10 Claims, No Drawings

METHOD FOR ENANTIOSELECTIVELY OPENING OXETAN-2-ONES

RELATED APPLICATIONS

This application is a national stage application (under 35 U.S.C. § 371) of PCT/EP2005/008190 filed Jul. 28, 2005, which claims benefit of German application 10 2004 037 700.6 filed Aug. 2, 2004 and German application 10 2004 038 589.0 filed Aug. 6, 2004.

The present invention relates to a method for preparing substantially enantiopure 3-hydroxy carboxylic acids or esters starting from racemic oxetan-2-ones.

Optically active 3-hydroxy carboxylic acids and their esters are intermediates in demand for preparing active ingredients for pharmaceutical applications.

PRIOR ART

The catalytic hydrogenation of ketones and ketoesters with Ru-diphosphine complexes is known (e.g. Burk et. al., J. Am. Chem. Soc 1995, 117, 4423; A. Mortreux et. al. Tetrahedron: Asymmetry, 7(2), 379-82, 1996; Noyori et. al. Angew. Chem., Int. Ed. Engl., 36(3), 285-288, 1997; WO 9713763 A1;

likewise known is the catalytic transfer hydrogenation of ketones with formic acid/triethylamine complex as reducing agent and ruthenium catalysts (P. Knochel et. al. Tetrahedron Lett., 37(45), 8165-8168, 1996; Sammakia et. al J. Org. Chem., 62(18), 6104-6105, 1997 (isopropanol as reducing agent).

It is common to these methods that catalysts and ligands which are very complicated to prepare are used. In the transfer hydrogenations, moreover, it is not low-cost hydrogen but isopropanol or formic acid/tert amines which is used. The latter interferes with the working up of the reaction and inevitably leads to the formation of acetone or carbon dioxide.

Moreover very large quantities of catalyst are generally used in the above studies; this makes previous processes uneconomic.

Sakai et al. (J. Chem. Soc., Perkin Trans. 1, 2000, 71-77) describes a lipase-catalyzed stereoselective transesterification of variously substituted oxetan-2-ones. However, the reactions under the described conditions are still not entirely satisfactory in relation to chemical and optical yield.

Statement of the Problem

The problem therefore was to provide methods for the enantioselective opening of oxetan-2-ones which eliminate the disadvantages of the prior art process and in particular ensure improved chemical yields and optical purities.

DESCRIPTION OF THE INVENTION

The present invention relates to a method for preparing substantially enantiopure 3-hydroxy carboxylic acids or esters of the general formula (III) by reacting racemic oxetan-2-ones of the general formula (I) with compounds $R^3$—OH of the general formula (II) in the presence of a lipase from *Candida antartica* or *Burkholderia plantarii*, and separating the resulting products of the formula (III) and (IV) fron one another

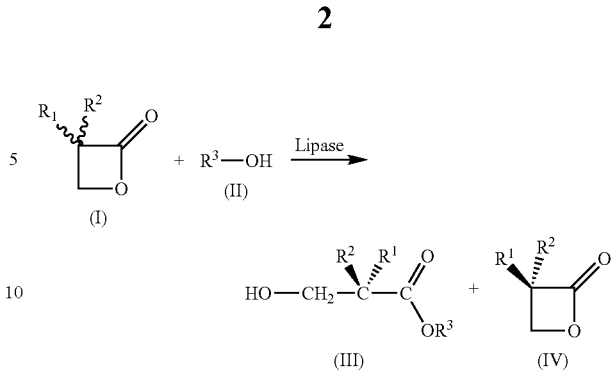

where the radicals have the following meaning:

$R^1$, $R^2$, $R^3$ independently of one another H; $C_1$-$C_{10}$-substituted or unsubstituted alkyl, substituted or unsubstituted aryl or hetaryl, where $R^1$ and $R^2$ may not simultaneously have the same meaning. The term "$C_1$-$C_{10}$-substituted or unsubstituted alkyl" also comprises cycloalkyls such as cyclopentyl, cyclohexyl, cycloheptyl, cyclopentylmethyl, cyclopentylethyl, cylcohexylmethyl, cyclohexylethyl.

The depicted formulae (III) and (IV) represent here one enantiomer in each case. However, the invention also includes the representation of the other enantiomer (antipode) (III) and (IV) in each case. The formation of the desired enantiomer can be influenced by the choice of the lipase.

Racemic oxetan-2-one of the general formula (I) are known in the literature and can easily be obtained by known methods—for example as described by Sakai et al. (J. Chem. Soc., Perkin Trans. 1, 2000, 71-77.

The compounds (II) are alcohols known to the skilled worker, and water. Depending on whether the desired 3-hydroxy carboxylic acids (III) are desired as free acids or directly as esters (II) is chosen to be water or alcohol.

Lipases suitable for the process of the invention are lipases from the organisms *Candida antartica* and *Burkholderia plantarii*. Microorganisms of the species *Burkholderia plantarii* are now also referred to as *Pseudomonas plantarii*.

Such microorganisms are known and can be obtained from public collections of strains, for example DSM No. 9509, DSM No. 7128, DSM No. 9510, ATCC No. 51545, NCPPB No. 3676, ATCC No. 43733, ICMP No. 9424, JCM No. 5492, LMG No. 9035.

A particularly suitable lipase can be obtained from the microorganism DSM No. 8246 (deposited on 28.04.1993). For the preparation of the lipase from this microorganism, reference is made to EP 1069183, especially Example 1, the contents of which are fully incorporated herein.

Microorganisms of the species *Candida antarctica* can be obtained from publicly accessible collections of strains, for example DSM No. 70725. Microorganisms of the species *Candida antarctica* are also classified under the name Pseudozyma aphidis (for example DSM No. 70725, ATCC No. 32657, CBS No. 6821, NRRL No. Y-7954).

A particularly suitable lipase from *Candida antarctica* is the lipase Novozym® 435 which is commercially available from Novozymes.

The lipase from *Burkholderia plantarii* prefers in the reaction of the invention the opposite stereochemistry to the lipase from *Candida antarctica* and is accordingly an ideal addition to the synthetic repertoire. The exact stereochemistry is evident from Examples 1 and 2.

The lipases can be employed for the method of the invention both as crude extract and in preparations of varying purity up to a highly purified form. In a preferred embodiment, the lipases have catalytic activities of 0.1-1000, preferably 10-400, particularly preferably 20-200, units per mg (measured as tributyrin units).

The lipase activity can be determined by known methods (Gupta et al. Review: Lipase assays for conventional and molecular screening: an overview., Biotechnol. Appl. Biochem. (2003) 37, 63-71), for example the titrimetric tributyrin assay.

A particularly preferred embodiment is the use of carrier-bound (immobilized) lipases. Such lipases and the methods for their immobilization are disclosed for example in EP 1069183 and the documents cited therein.

The radicals $R^1$, $R^2$, and $R^3$ in the formulae (I) to (IV) mean hydrogen, $C_1$-$C_{10}$-substituted or unsubstituted alkyl, substituted or unsubstituted aryl or heteroaryl. Unsubstituted alkyl means here in particular methyl, ethyl, n- and isopropyl, n-, iso-, tert-butyl, straight-chain and branched pentyl, hexyl, heptyl, octyl, nonyl and decyl, and the branched alkyls for example cyclobutane, cyclopentane, cyclohexane. Substituted alkyl means here a radical in which, by comparison with the corresponding unsubstituted alkyl radical, one or more H atoms are replaced by other atoms or molecular groups such as $NH_2$, N(alkyl)H, N(alkyl)$_2$, OH, O-alkyl, SH, S-alkyl, CN, $NO_2$, I; Cl, Br, F, carbonyl, carboxyl, ester, aryl or hetaryl. Substituted alkyls also include from the definition mono- or polyunsaturated alkyls such as alkenes and alkynes.

Unsubstituted aryls are in particular phenyl and naphthyl, unsubstituted hetaryls are aromatic compounds in which at least one C atom is replaced by a so-called heteroatom such as O, N, S. Preferred hetaryls are pyrryl, furyl, thiophenyl, pyridyl, pyrimidyl.

The radicals $R^1$ and $R^2$ may not, however, simultaneously have the same meaning, because otherwise no optically active C atom results, and fractionation of the racemate (I) is inapplicable.

The method of the invention can be carried out with or without solvent. A solvent is, however, preferably used, in particular from the group of alkyl ethers, or the precursor (II) is as additionally also employed as solvent. Methyl tert-butyl ether and diisopropyl ether is particularly preferably employed as solvent.

A reaction competing with the ring opening of the oxetan-2-one (I) with the alcohol (II) is the ring opening of (I) by (III) or else the transesterification of (III) with a further molecule of (III), resulting in "dimer formation" of (III). In order to suppress these unwanted competing reactions as far as possible, it is advisable to work with a solvent, if appropriate with the alcohol (III) as solvent. A solvent is particularly preferably used in an amount of up to 25% by weight based on (I).

Since no lipase operates 100% stereoselectively, there is always formation of a certain proportion of the unwanted enantiomer as 3-hydroxy carboxylic acid or ester (III) with an appropriately long reaction time. The reaction time chosen for the reaction is therefore a compromise between reaction yield and optical purity of the products. Long reaction times usually lead to high yields at the expense of the optical purity, whereas shorter reaction times lead to high optical purities of the products but at the expense of the overall yield. Depending on the nature of the reactants and the chosen conditions, it is therefore advisable for the reaction kinetics to be recorded in exploratory preliminary tests and for the optimal reaction time to be inferred therefrom.

The reaction time of the enzyme-catalyzed reaction also depends very greatly on the chosen temperature. The reaction can be carried out in a wide temperature range, preferably at temperatures at which the lipase used is sufficiently active. Preferred temperatures are between 5 and 70, in particular between 10 and 50° C.

The reaction can be carried out either continuously or batchwise. Continuous synthesis, especially using a supported lipase, is recommended for performance on the industrial scale.

After the precursors (I) and (II) have reacted, the products (III) and (IV) are present together. Separation of the products (III) and (IV) is possible by conventional means because of the difference in the chemical structure. Distillation methods or extraction methods are preferably used for the separation. If (III) is in the form of the acid ($R^3$=H), it is possible and preferred for (III) to be separated in the form of its alkali metal or ammonium salt from (IV).

The unwanted enantiomer (IV) can also be returned after racemization into the reaction mixture. However, it is also possible to obtain from (IV) the corresponding 3-hydroxy carboxylic acid or ester (III) by hydrolysis with retention of the optically active center.

The present invention can also be used for preparing substantially enantiopure oxetan-2-ones of the general formula (IV).

The invention thus further relates to a method for preparing substantially enantiopure oxetan-2-ones of the general formula (IV) by reacting racemic oxetan-2-ones of the general formula (I) with compounds $R^3$—OH of the general formula (II) in the presence of a lipase from *Candida antartica* or *Burkholderia plantarii*, and separating the resulting products of the formula (III) and (IV) from one another

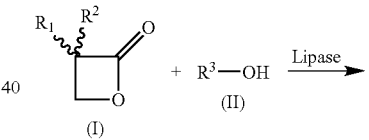

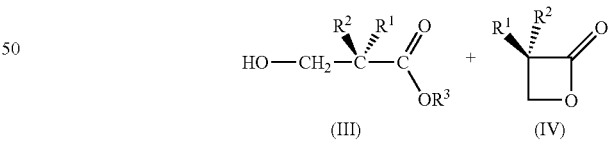

where the radicals have the following meaning:

$R^1$, $R^2$, $R^3$ independently of one another H; $C_1$-$C_{10}$-substituted or unsubstituted alkyl, substituted or unsubstituted aryl or hetaryl, where $R^1$ and $R^2$ may not simultaneously have the same meaning. The term "$C_1$-$C_{10}$-substituted or unsubstituted alkyl" also comprises cycloalkyls such as cyclopentyl, cyclohexyl, cycloheptyl, cyclopentylmethyl, cyclopentylethyl, cylcohexylmethyl, cyclohexylethyl.

EXPERIMENTAL SECTION

Example 1

Reaction Using *Candida antarctica* Lipase

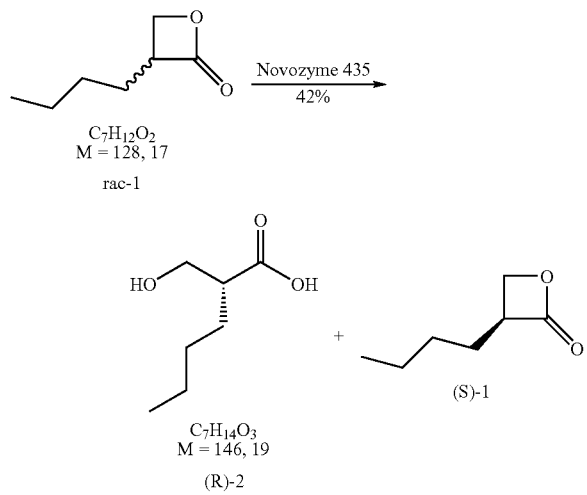

| Apparatus: | 4000 ml BASF-Miniplant stirred vessel, 3-paddle metal propellor stirrer (d = 10 cm) with 4 baffles, 164 rpm, thermostats internal temperature controlled |
|---|---|
| Mixture: | |
| 3-Butyl-oxetan-2-one (6) | 121 g (0.95 mol) |
| Methyl tert-butyl ether | 1200 ml (reaction) |
| | 4300 ml (extraction) |
| Novozym 435 | 1.94 g (1.6%) |
| Deionized water | 10.05 ml (0.56 mol) |
| $NaHCO_3$ solution (10%) | 795 ml (0.95 mol) |
| Sulfuric acid (50%) | 111.3 g (0.57 mol) |
| Procedure: | |
| 121 g (0.95 mol) | of rac-lactone 6 are introduced into |
| 1200 ml | of methyl tert-butyl ether, and |
| 1.94 g (1.6%) | of Novozym ®435 are added, followed by |
| 10.05 ml (0.56 mol) | of deionized water. |
| | Stir at 25.0° C. for 17 h. |
| | Filtration of the enzyme. |
| | Washing of the organic solution with |
| 795 ml | of $NaHCO_3$ solution (10%), pH 8.65 |
| | Phase separation |
| | Back-extraction with |
| 2× 800 ml | of methyl tert-butyl ether |
| | Phase separation |
| | Combine all 3 organic phases. (Lactone) |
| | Acidify aqueous phase with $H_2SO_4$ |
| | (pH <3.0) and extract |
| | three times with |
| (3×) 900 ml | of methyl tert-butyl ether. |
| | Combine all 3 organic phases. (Acids) |
| | Drying over sodium sulfate. Filtration. |
| | The solvent is removed in a rotary evaporator. |
| Yield: | Acid = 58.2 g    chiral HPLC (GKA): |
| | (0.40 mol), 42%    >99% ee |
| | Lactone = 70.0 g    chiral GC (GVF-C): |
| | (0.55 mol), 58%    80.03% |
| | Chiral conversion = 44.7% |

Example 2

Reaction Using *Burkholderia plantarii* Lipase (DSM 8246))

Under the same conditions as in Example 1—although a lipase from *Burkholderia plantarii* was used instead of Novozym® 435 (40 mg, 75 U/mg (tributyrin units)—products having the opposite stereochemistry were obtained. (S)-2 (0.85 g; 5.6 mmol; 37%; 94ee) and (R)-1 (1.08 g; 8.2 mmol; 54%; 95ee) were obtained from rac-1 (2 g, 15.60 mmol).

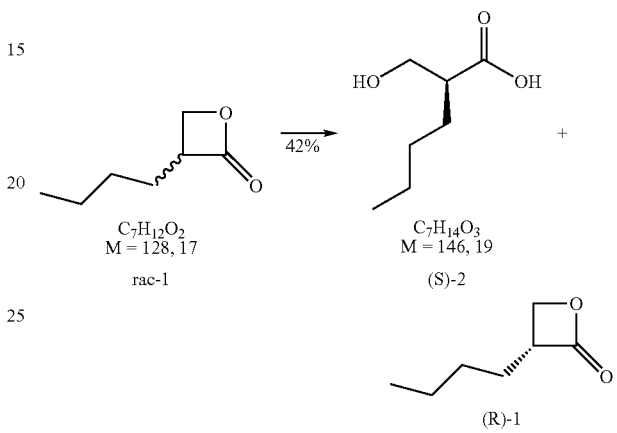

Example 3

Reaction of Various Substituted oxetan-2-ones Using *Candida antarctica* and *Burkholderia plantarii* Lipases The substrates of the general formula (I) which are mentioned in the table below were reacted in analogy to Example 1 and 2, and the corresponding acids of the general formula (III) ("R or S acid") or oxetan-2-ones of the general formula (IV) ("R and S lactone") were obtained with the stated stereochemistry.

| Enzyme | $R^2$ = Me, $R^1$ = H | $R^2$ = Et, $R^1$ = H | $R^2$ = n-Pr, $R^1$ = H | $R^2$ = i-Pr, $R^1$ = H |
|---|---|---|---|---|
| Novozym ® 435 | 98.5% ee R acid | 99% ee R acid | 99% ee R acid | 99% ee R acid |
| | 99% ee S lactone | 98% ee S lactone | 98% ee S lactone | 99% ee S lactone |
| Lipase BP (DSM 8246) | 98% ee S acid | 97.5% ee S acid | 99% ee S acid | 99% ee S acid |
| | 98% ee R lactone | 98% ee R lactone | 97% ee R lactone | 99% ee R lactone |

We claim:

1. A method for preparing substantially enantiopure 3-hydroxy carboxylic acids or esters of the formula (III) and/or substantially enantiopure oxetan-2-ones of the formula (IV) comprising the steps of
    (1) reacting racemic oxetan-2-ones of the general formula (I) with compounds of the general formula (II) in the presence of a lipase from *Candida antarctica* or *Burkholderia plantarii*, and
    (2) separating the resulting products of formulae (III) and (IV) from one another

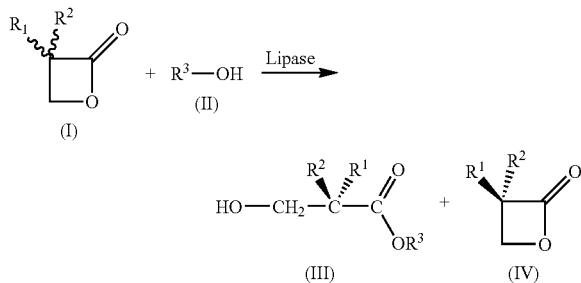

wherein $R^1$, $R^2$, and $R^3$ are, independently of one another, H, $C_1$ to $C_{10}$ substituted or unsubstituted alkyl, or substituted or unsubstituted aryl or heteroaryl, with the proviso that $R^1$ cannot equal $R^2$.

2. The method according to claim 1, wherein $R^1$ is H and $R^2$ is selected from the group consisting of n-butyl, methyl, ethyl, isopropyl, and phenyl.

3. The method according to claim 1, wherein the reaction of step (1) is carried out in the presence of methyl tert-butyl ether.

4. The method according to claim 1, wherein said lipase is carrier-bound.

5. The method according to claim 1, wherein the reaction of step (1) is carried out continuously.

6. The method according to claim 1, wherein the separation of step (2) is accomplished by distillation, extraction or a combination thereof.

7. The method according to claim 2, wherein the reaction of step (1) is carried out in the presence of methyl tert-butyl ether.

8. The method according to claim 7, wherein said lipase is carrier-bound.

9. The method according to claim 8, wherein the reaction of step (1) is carried out continuously.

10. The method according to claim 9, wherein the separation of step (2) is accomplished by distillation, extraction or a combination thereof.

* * * * *